(12) United States Patent
McNall, III et al.

(10) Patent No.: US 10,702,650 B2
(45) Date of Patent: Jul. 7, 2020

(54) STERILE ASSEMBLED LIQUID MEDICAMENT DOSAGE CONTROL AND DELIVERY DEVICE

(71) Applicant: BioQ Pharma Incorporated, San Francisco, CA (US)

(72) Inventors: Ralph I. McNall, III, Belmont, CA (US); Joshua W. Kriesel, San Francisco, CA (US); Thomas T. Donze, San Bruno, CA (US)

(*) Notice: Subject to any disclaimer, the term of this patent is extended or adjusted under 35 U.S.C. 154(b) by 290 days.

(21) Appl. No.: 15/968,150

(22) Filed: May 1, 2018

(65) Prior Publication Data

US 2018/0243500 A1 Aug. 30, 2018

Related U.S. Application Data

(62) Division of application No. 14/593,720, filed on Jan. 9, 2015, now Pat. No. 9,987,416.

(51) Int. Cl.
*A61M 39/16* (2006.01)
*A61M 5/142* (2006.01)
(Continued)

(52) U.S. Cl.
CPC ........ *A61M 5/142* (2013.01); *A61M 5/14232* (2013.01); *A61M 39/18* (2013.01);
(Continued)

(58) Field of Classification Search
CPC .................. A61M 5/142; A61M 39/18; A61M 2039/1022; A61M 5/5086;
(Continued)

(56) References Cited

U.S. PATENT DOCUMENTS 3,909,910 A 10/1975 Rowe et al.
4,019,512 A 4/1977 Tenczar
(Continued)

FOREIGN PATENT DOCUMENTS

JP S49129223 12/1974
JP S63230175 A 9/1988
WO 2011002853 A2 1/2011

*Primary Examiner* — Manuel A Mendez
*Assistant Examiner* — Courtney B Fredrickson
(74) *Attorney, Agent, or Firm* — Thomas W. Galvani, P.C.; Thomas W. Galvani

(57) ABSTRACT

A method of assembling a liquid medicament dispenser, includes the step of providing a housing, a reservoir, a tubing set, an administration line, an aseptic connector assembly having upstream and downstream portions, and a pump. The upstream portion of the aseptic connector assembly is coupled to the reservoir, and the reservoir is filled with a liquid medicament. The downstream portion of the aseptic connector assembly is coupled to the tubing set. The reservoir and the upstream portion of the aseptic connector assembly are sterilized together. The downstream portion of the aseptic connector assembly, the tubing set, and the administration line are sterilized together. The upstream portion of the aseptic connector assembly is connected to the downstream portion of the aseptic connector assembly, and the reservoir, pump, and other elements are mounted in the housing.

6 Claims, 6 Drawing Sheets

(51) Int. Cl.
  *A61M 39/18* (2006.01)
  *A61M 39/10* (2006.01)
  *A61M 5/168* (2006.01)
(52) U.S. Cl.
  CPC ..... *A61M 5/14244* (2013.01); *A61M 5/16854* (2013.01); *A61M 2039/1022* (2013.01); *A61M 2039/1072* (2013.01)
(58) Field of Classification Search
  CPC .......... A61M 5/14232; A61M 5/14248; A61M 5/16854; A61M 5/168; A61M 2039/0285
  See application file for complete search history.

(56) References Cited

U.S. PATENT DOCUMENTS

| | | | |
|---|---|---|---|
| 4,137,913 A | 2/1979 | Georgi | |
| 4,861,335 A | 8/1989 | Reynolds | |
| 5,244,463 A | 9/1993 | Cordner et al. | |
| 5,324,258 A | 6/1994 | Rohrbough | |
| 5,538,399 A * | 7/1996 | Johnson | A61M 5/142 417/53 |
| 5,906,589 A | 5/1999 | Gordon et al. | |
| 6,109,895 A | 8/2000 | Ray et al. | |
| 6,655,655 B1 * | 12/2003 | Matkovich | A61M 39/1011 251/149.1 |
| 6,835,049 B2 | 12/2004 | Ray | |
| 7,169,128 B2 | 1/2007 | Kriesel et al. | |
| 7,220,244 B2 | 5/2007 | Kriesel | |
| 7,220,245 B2 | 5/2007 | Kriesel | |
| 7,316,245 B2 | 1/2008 | Bivin | |
| 7,470,253 B2 | 12/2008 | Kriesel et al. | |
| 7,481,244 B2 | 1/2009 | Bivin | |
| 7,513,273 B2 | 4/2009 | Bivin | |
| 7,694,938 B2 | 4/2010 | Kriesel et al. | |
| 7,735,522 B2 | 6/2010 | Bivin et al. | |
| 7,776,006 B2 | 8/2010 | Childers et al. | |
| 7,789,853 B2 | 9/2010 | Kriesel | |
| 7,828,770 B2 | 11/2010 | Bivin et al. | |
| 7,828,772 B2 | 11/2010 | Kriesel et al. | |
| 7,833,195 B2 | 11/2010 | Kriesel et al. | |
| 7,837,653 B2 | 11/2010 | Kriesel et al. | |
| 7,896,843 B2 | 3/2011 | Kriesel et al. | |
| D636,271 S | 4/2011 | Kriesel | |
| 7,993,304 B2 | 8/2011 | Kriesel et al. | |
| 8,029,468 B2 | 10/2011 | Kriesel et al. | |
| 8,057,435 B2 | 11/2011 | Kriesel et al. | |
| 8,083,503 B2 | 12/2011 | Voltenburg, Jr. et al. | |
| 8,083,717 B2 | 12/2011 | Kriesel | |
| 8,100,890 B2 | 1/2012 | Kriesel et al. | |
| 8,105,280 B2 | 1/2012 | Iddan et al. | |
| 8,114,052 B2 | 2/2012 | Bivin et al. | |
| 8,123,723 B2 | 2/2012 | Bivin et al. | |
| 8,133,204 B1 | 3/2012 | Kriesel | |
| 8,142,398 B1 | 3/2012 | Kriesel et al. | |
| 8,197,445 B2 | 6/2012 | Kriesel et al. | |
| 8,211,059 B2 | 7/2012 | Kriesel et al. | |
| 8,226,609 B2 | 7/2012 | Kriesel et al. | |
| 8,231,575 B2 | 7/2012 | Kriesel | |
| 8,287,521 B2 | 10/2012 | Kriesel et al. | |
| 8,292,848 B2 | 10/2012 | Kriesel et al. | |
| 8,292,876 B2 | 10/2012 | Kriesel et al. | |
| 8,317,753 B2 | 11/2012 | Kriesel et al. | |
| 8,361,009 B2 | 1/2013 | Lee et al. | |
| 8,377,043 B2 | 2/2013 | Kriesel et al. | |
| 8,388,571 B2 | 3/2013 | Joshi et al. | |
| 8,388,578 B2 | 3/2013 | Joshi et al. | |
| 8,403,887 B2 | 3/2013 | Kriesel et al. | |
| 8,480,656 B2 | 7/2013 | Kriesel | |
| 8,622,965 B2 | 1/2014 | Kriesel | |
| 8,672,885 B2 | 3/2014 | Kriesel et al. | |
| 8,821,454 B2 | 9/2014 | Kriesel et al. | |
| 2003/0030272 A1 | 2/2003 | Johnson et al. | |
| 2005/0151105 A1 | 7/2005 | Ryan et al. | |
| 2006/0030838 A1 | 2/2006 | Gonnelli | |
| 2006/0052322 A1 | 3/2006 | Roth et al. | |
| 2007/0235083 A1 | 10/2007 | Glugos | |
| 2009/0093793 A1 | 4/2009 | Gross et al. | |
| 2009/0124994 A1 | 5/2009 | Roe | |
| 2010/0021230 A1 * | 1/2010 | Olivier | A61M 39/10 403/11 |
| 2011/0282284 A1 | 11/2011 | Kriesel et al. | |
| 2011/0282300 A1 | 11/2011 | Kriesel et al. | |
| 2012/0130341 A1 | 5/2012 | Whitley | |
| 2013/0218123 A1 | 8/2013 | Beiriger | |
| 2013/0296792 A1 | 11/2013 | Cabiri | |
| 2013/0296803 A1 | 11/2013 | Kriesel | |
| 2013/0331823 A1 | 12/2013 | Askem et al. | |
| 2014/0058318 A1 | 2/2014 | Yodfat et al. | |
| 2014/0213975 A1 | 7/2014 | Clemente et al. | |
| 2014/0241923 A1 | 8/2014 | Nzike et al. | |
| 2014/0296787 A1 | 10/2014 | Agard et al. | |
| 2014/0301913 A1 | 10/2014 | Williams et al. | |
| 2015/0174304 A1 | 6/2015 | Askem et al. | |
| 2016/0144094 A1 | 5/2016 | Margolin et al. | |

* cited by examiner

STERILE ASSEMBLED LIQUID MEDICAMENT DOSAGE CONTROL AND DELIVERY DEVICE

CROSS-REFERENCE TO RELATED APPLICATIONS

This application is a divisional of and claims the benefit of prior U.S. patent application Ser. No. 14/593,720, filed Jan. 9, 2015, which is hereby incorporated by reference.

FIELD OF THE INVENTION

The present invention relates generally to medical equipment, and more particularly to devices for controlling and dispensing medicament to a patient.

BACKGROUND OF THE INVENTION

Precise infusion of large volumes of liquid medicament through an administration line is usually accomplished by an infusion pump. Traditional infusion pumps make use of a flexible infusion bag suspended above the patient. For many medicaments and drugs, a pharmacist, nurse, doctor, or other medical professional is required to prepare the infusion bag by reconstituting, diluting, and/or mixing the medicament or drug in preparation for its delivery and use with a pump. Such methods are cumbersome, imprecise, require many time-consuming steps by medical professionals, are susceptible to medication errors and require bed confinement of the patient. Periodic monitoring of the apparatus by a nurse, doctor, or other medical professional is required to detect malfunctions of the infusion pump. Accordingly, over the years, infusion pumps developed into increasingly more complex devices which are expensive and sophisticated. Such devices include a large number of features, options, and programmability possibilities. While those capabilities can be advantageous in providing a range of customization to medicament administration, they also lead to use error, and the possibility of patient harm, injury, or death.

Complicated infusion pumps also typically require many time-consuming steps for setup, including applying both a medicament reservoir and administration line to the pump. Increased preparation requirements increase the risk of contaminating the pump, the medicament reservoir, the administration line, or other elements of the intravenous line system. An improved system for providing a convenient and sterile infusion of large volumes of medicament is needed.

SUMMARY OF THE INVENTION

A liquid medicament dosage control and delivery device includes an aseptic fluid communication path from a liquid medicament reservoir to an administration line that can be stored and delivered without risk of contamination. The reservoir of the device is filled with a liquid medicament and sterilized before assembly into the device. The fluid communication path includes a tubing set and the administration line which are also sterilized and then coupled to the pre-filled reservoir with an aseptic connector that prevents contamination. The aseptic connector includes a barrier preventing liquid medicament from flowing into the tubing set until the barrier is removed. Removal of the barrier from the aseptic connector both couples the reservoir in fluid communication with the tubing set and energizes the device with power so that the device may be used to safely deliver contaminant-free liquid medicament to a patient.

BRIEF DESCRIPTION OF THE DRAWINGS

Referring to the drawings.

DETAILED DESCRIPTION

Figure 1:
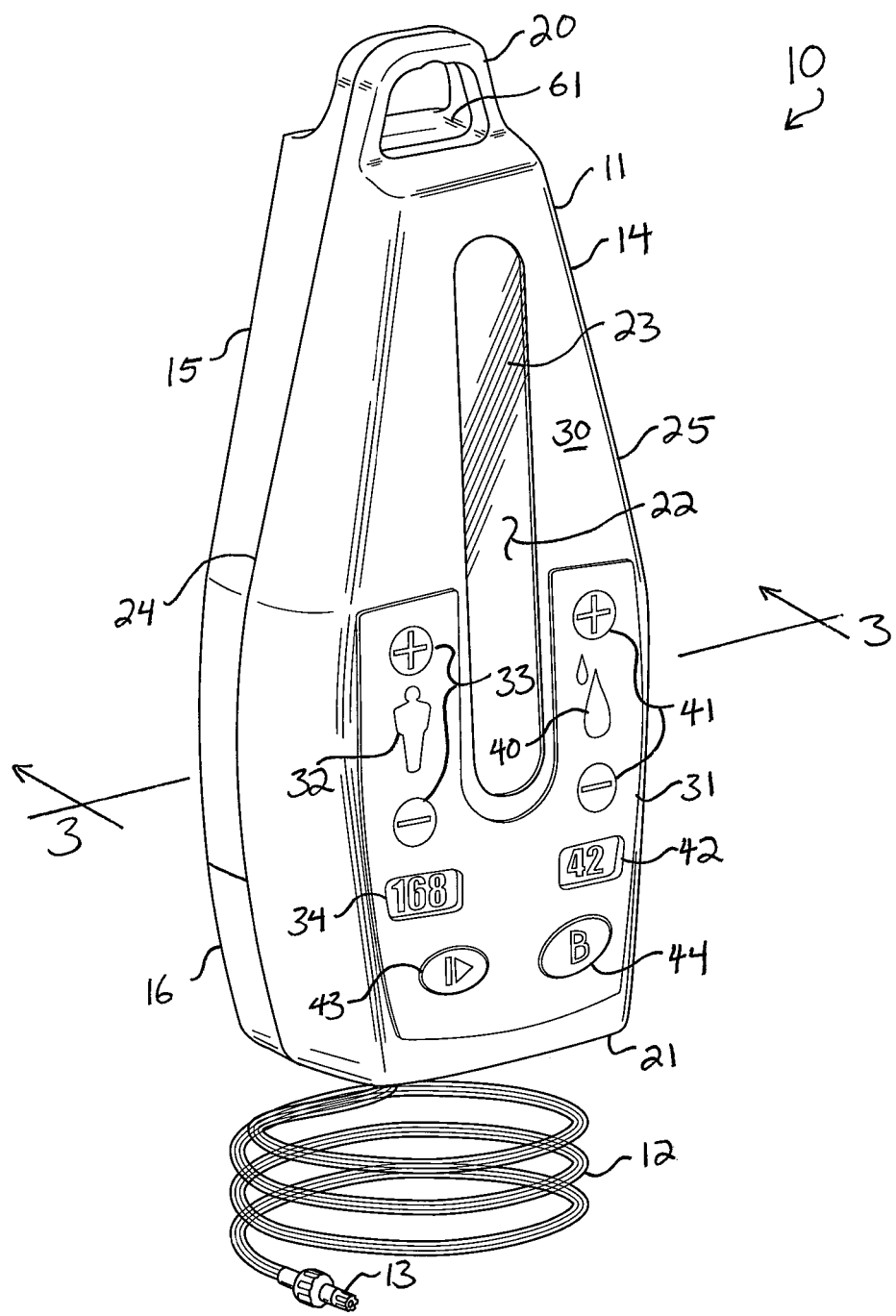
FIG. 1 is a front perspective view of a sterile assembled liquid medicament dosage control and delivery device.

Reference now is made to the drawings, in which the same reference characters are used throughout the different figures to designate the same elements. FIG. 1 illustrates a front perspective view of a sterile assembled liquid medicament dosage control and delivery device 10 (hereinafter, the "device 10") useful for delivering a liquid medicament (hereinafter referred to both as the "medicament" and the "liquid medicament") to a patient via an administration line at a controlled rate set according to several parameters. The device 10 consists of a housing 11 containing a medicament reservoir coupled to a pump to draw medicament from the reservoir and communicate it through an administration line 12 to a capped coupling 13, which typically interfaces with a conventional intravenous line for application to a patient. The device 10 is preferably a single-use, disposable, and aseptically presented dispenser with a sterile, pre-filled medicament, which is ready use without the need for assembly or complicated programming, thus helping to prevent use error, infection, injury, and even death.

The housing 11 has a generally teardrop shape and, in the embodiment shown in FIG. 1, is constructed from three sections or panels: a front panel 14, a rear top panel 15, and a rear bottom panel 16, each of which is coupled together such as by snap tab fittings, adhesive, sonic welding, screws or like fastening method suitable for a sterilized enclosure. The front panel 14 is a single, monolithic piece extending from a top 20 of the device 10 to a bottom 21 of the device 10. For purposes of clarity of description, the term "axial" will be used herein to describe various structural elements or features extending generally between the top 20 and the bottom 21 or parallel to a line oriented between the top 20 and the bottom 21. Briefly, a hook 61 formed at the top 20 of the device 10 between the front and rear top panels 14 and 15 allows the device 10 to be hung so that the axial direction also corresponds with a vertical, or plumb alignment of the device 10 in which the bottom 21 is directly below the top 20. For this reason, and for purposes of orientation, the relative location of structural elements and features may be described in terms of "above" or "upward" and "below" or "downward," though it should be understood that the device 10 does not need to be arranged in a bottom 21-down orientation as if the device 10 were hung from the hook 61 for proper function.

The front panel 14 is formed with an axial slot defining a window 22 through the housing 10 in which a medicament reservoir 23 (referred to hereinafter as both "reservoir 23" and "medicament reservoir 23") carried inside the device 10 is observable. The window 22 is located between opposed sides 24 and 25 of the device 10 and extends from proximate the top 20 of the device to a location intermediate between the top 20 and bottom 21. The window 22 has parallel sides and a curved top and curved bottom.

The front panel 14 has a flat face 30 on which is mounted a panel 31 carrying control information for displaying and controlling the operation of the device 10. The panel 31 surrounds a lower portion of the window 22 and extends between the sides 24 and 25 and from a location intermediate between the top 20 and bottom 21 to the bottom 21. Proximate to the side 24 (which may be referred to herein as "the left side 24"), the panel 31 includes a first icon 32 grouped together with a pair of buttons 33. The first icon 32, in the embodiment shown in FIG. 1, preferably represents weight, and the pair of buttons 33 increment and decrement a weight value shown in the display 34. In use, the weight value is that of the patient. The icon 32, the pair of buttons 33, and the window 34 are each aligned axially with each other proximate to the side 24 of the device. Alternatively, the pair of buttons 33 and display 34 can correspond to patient surface area, a common dosing measurement in medicine. The button 33 corresponding to increment the value is disposed above the icon 32, and the button 33 corresponding to decrementing the value is disposed below the icon 32. The window 34 is below both the icon 32 and the pair of buttons 33.

Proximate to the side 25 (which may be referred to herein as "the right side 25"), the panel 31 includes a second icon 40 grouped together with a pair of buttons 41. The second icon 40, in the embodiment shown in FIG. 1, preferably represents dosage, and the pair of buttons 41 increment and decrement a dosage to be supplied to the patient and shown in the display 42. The icon 40, the pair of buttons 41, and the window 42 are each aligned axially with each other proximate to the side 25 of the device. The button 41 corresponding to increment the dosage is disposed above the icon 40, and the button 41 corresponding to decrementing the dosage is disposed below the icon 40. The window 42 is below both the icon 40 and the pair of buttons 41. The icon 32 and pair of buttons 33 are thus opposed from the icon 40 and pair of buttons 41, and together flank the window 22. Further carried on the panel are a start/stop button 43 and a bolus control button 44. The start/stop button 43 is proximate to the left side 24 and below the window 34, and the bolus control button 44 is proximate to the right side 25 and below the window 42.

Figure 2:
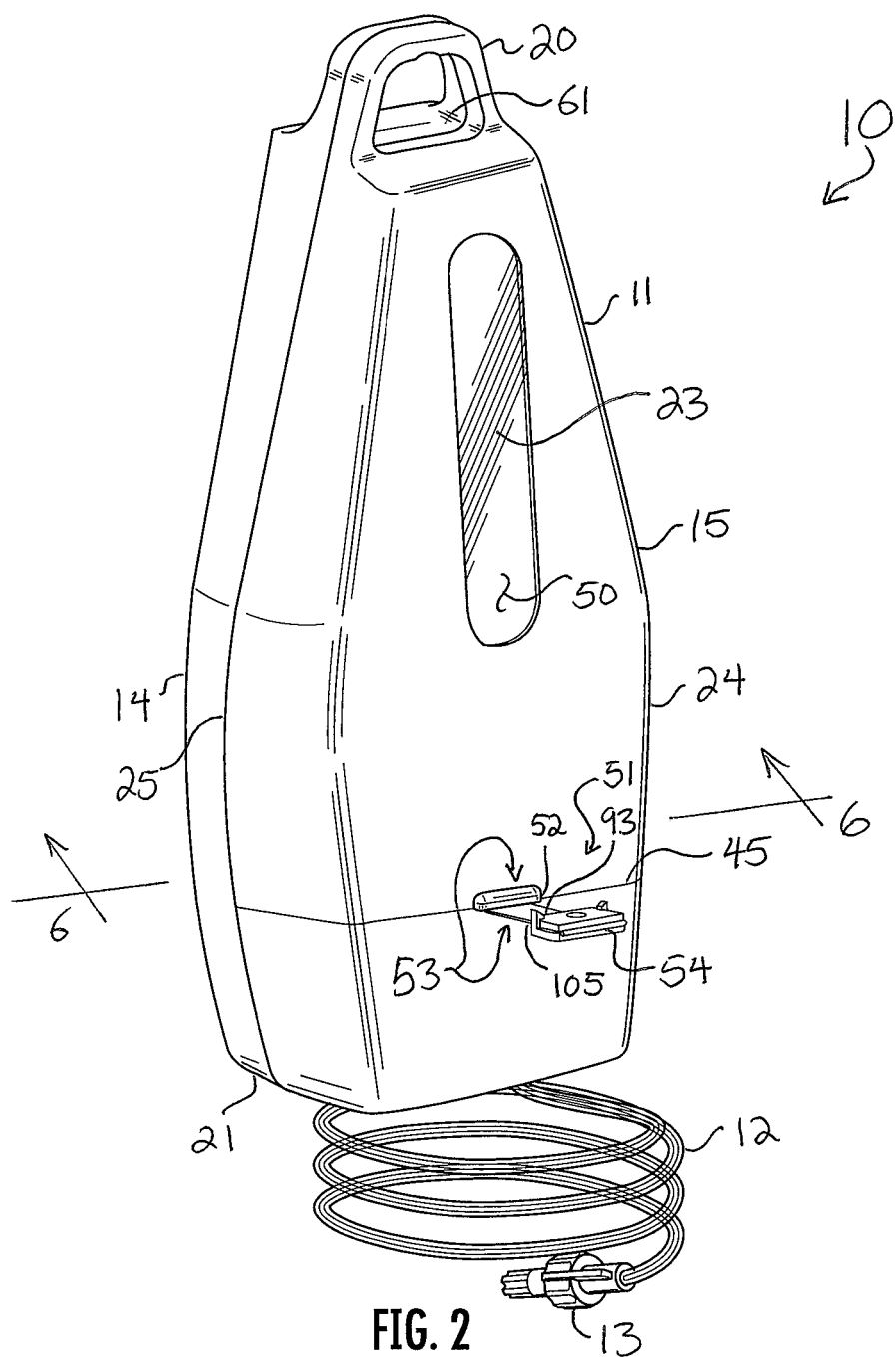
FIG. 2 is a rear perspective view of the device of FIG. 1.

Turning to FIG. 2, which illustrates a rear perspective view of the device 10, the rear top and rear bottom panels 15 and 16 are clearly shown. The rear top panel 15 is a single, monolithic piece extending from the top 20 of the device 10 to a seam 45 defined between the rear top and rear bottom panels 14 and 15. The rear bottom panel 16 is a single, monolithic piece extending from the seam 45 to the bottom 21 of the housing 11; thus the rear of the device 10 is preferably formed by two panels joined together. One having ordinary skill in the art will readily appreciate that the rear of the device 10, and that the housing 11 of the device 10, indeed, is, in other embodiments, formed by a single panel or multiple panels. Shown throughout the drawings is a preferred embodiment, but not a limiting embodiment. Preferably, the housing 11, and each of the front, rear top, and rear bottom panels 14, 15, and 16 are formed by a material or combination of materials having the characteristics of rigidity, strength, durability, and light weight, such as plastic.

An axially-extending slot defining a window 50 is formed through the rear top panel 15 in which the medicament reservoir 23 carried inside the device 10 is observable. The window 50 is located between opposed sides 24 and 25 of the device 10 and extends from proximate the top 20 of the device to a location intermediate between the top 20 and the seam 45. The window 22 has parallel sides and a curved top and curved bottom. The reservoir 23 is preferably transparent or translucent, allowing a user to see entirely through the reservoir 23 through the housing 10 at the windows 22 and 50, or allowing the reservoir 23 to be backlit through one of the windows 22 or 50.

The seam 45 is formed between abutting edges of the rear top and rear bottom panels 15 and 16, which may overlap in a snap-fit or other engagement. A pull assembly 51 is routed through the housing 10 and threaded through a slit 52 formed at an intermediate location in the seam 45 of the housing 10. The pull assembly 51 includes a two-ply ribbon 53 extending from within the housing where the two-ply ribbon 53 is coupled mechanically and electrically to irreversibly arrange the device 10 from a storage state to an operation state, as will be explained in detail below. Arranging the aseptic connector assembly 63 from the storage state to the use state is irreversible. The pull assembly 51 further includes a pull tab 54 at the distal end of the two-ply ribbon 53.

Figure 3:
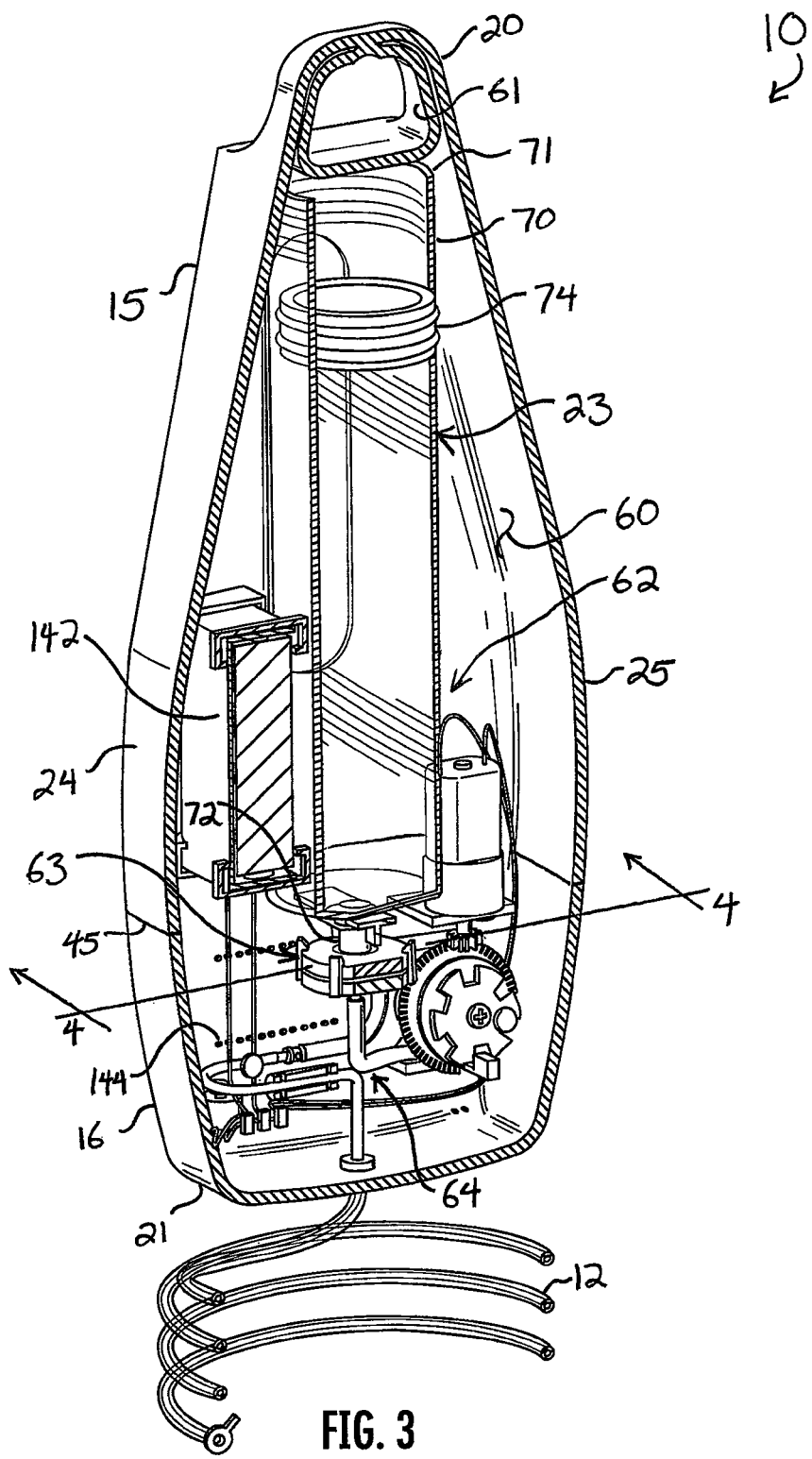
FIG. 3 is a section view of the device of FIG. 1 taken along the line 3-3 in FIG. 1.

Turning now to FIG. 3, which is a section view taken along the line 3-3 in FIG. 1, an interior 60 of the device 10 is shown. The interior 60 is a single compartment defined cooperatively between the front panel 14 (not shown) and the rear top and bottom panels 15 and 16 and contains mechanisms for running and operating the device 10. The interior 60 is a protective environment which protects the various structural elements and features carried within from impact, penetration, tampering, and other possibly damaging forces.

A fluid communication path 62 is carried by the device 10 to deliver liquid medicament to a patient. The fluid communication path 62 has a number of components including, from an upstream to a downstream location, the medicament reservoir 23, an aseptic connector assembly 63, a tubing set 64, and the administration line 12. The fluid communication path 62 is a sterile pathway for delivering liquid medicament to a patient, and maintains a sterile pathway during storage, distribution, shipping, delivery, preparation, and setup for use with a patient. The fluid-contacting portions, or the internal portions, of each of the components of the fluid communication path 62, namely, the medicament reservoir 23, an aseptic connector assembly 63, a tubing set 64, and the administration line 12 are sterilized prior to assembly, and the device 10 are assembled carefully to maintain the fluid-contacting portions in an aseptic manner, so that the device 10 provides for delivering a unit-dose of the medicament to a patient safely. Preferably, and as described in detail later, the medicament reservoir 23 containing the medicament and a portion of the aseptic connector assembly 63 are sterilized separately from another portion of the aseptic connector assembly 63, the tubing set 64, and the administration line 12, and the fluid communication path 62 is then assembled into the housing 11 with the other various structural elements and features carried by the housing which interact with the fluid communication path 62 to store, power, operate, and control the device 10.

Still referring to FIG. 3, the medicament reservoir 23 is disposed intermediately between the sides 24 and 25 and just below the hook 61 at the top 20. The medicament reservoir 23 shown in FIG. 3 is an inverted pre-filled cartridge or syringe having a barrel 70 extending axially from just below the hook 61 to approximately the seam 45 between the rear top and bottom panels 15 and 16. "Pre-filled" is used here to mean that the medicament is applied to the medicament reservoir 23 before assembly of the medicament reservoir 23 into the housing 11 and before the medicament reservoir 23 is coupled to any other structural element or feature of the device 10. The barrel 70 is a transparent or translucent cylindrical compartment, preferably having graduated volume indication lines arranged axially along the barrel, and holding between 20 to 300 milliliters and preferably between 30 and 100 milliliters. The barrel 70 has an open top 71 and a tip 72 directed downward. The tip 72 is more clearly seen in FIG. 4; looking briefly to that drawing, it can be seen that the tip 72 is open and has an inwardly-formed helical thread 73 and receives a post 83 therein for communicating the medicament out of the reservoir 23 downstream. Returning to FIG. 3, a piston 74 is snug fit within the barrel 70, so mounted for sliding movement downward from the top 71 to the tip 72 in response to a drawing off of the medicament in the reservoir 23 as the medicament is delivered through the fluid communication path 62 to the patient. The piston 74 is constructed from a material or combination of materials having characteristics of inertness, low permeability, durability, and compressibility, such as isoprene, chlorobutyl, bromobutyl, natural and synthetic rubber compounds, as well as thermoplastic elastomers. In some embodiments, the piston 74 is coated in silicone, polytetrafluoroethylene ("PTFE") or other similar coating to improve the sliding movement against friction between the piston 74 and the barrel 70. The medicament is, of course, contained by the barrel 23 between the piston 74 and the tip 72. The medicament is not shown in the drawings, as one having ordinary skill in the art will readily appreciate its flow through the device 10. With the top 71 of the barrel 70 open, as the piston 74 is drawn downward toward the tip 72, no pressure or back pressure is created which would tend to draw the piston 74 backward toward the top 71.

Figure 4:
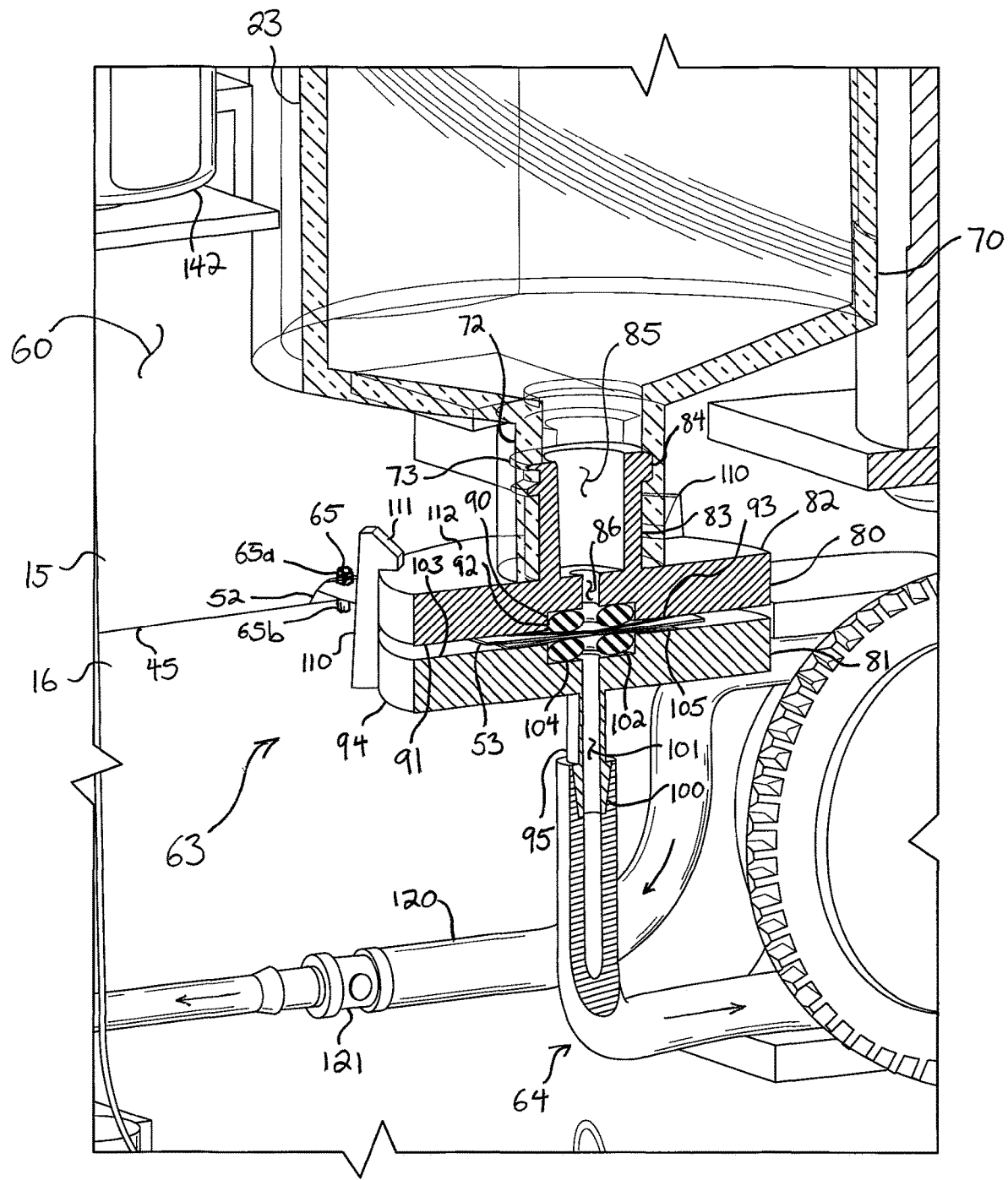
FIG. 4 is an enlarged section view of the device of FIG. 1 taken along the line 4-4 in FIG. 3.

Coupled to the tip 72 of the reservoir 23 is the aseptic connector assembly 63, best seen in the enlarged view of FIG. 4. The aseptic connector assembly 63 is a generally two-part assembly including an upstream or upper aseptic connector 80 and a downstream or lower aseptic connector 81 assembled with a barrier disposed therebetween. The upper and lower aseptic connectors 80 and 81 are first and second—or upstream and downstream—portions of the aseptic connector assembly 63; identification as such is non-limiting and not meant to indicate that there are only or exactly two portions of the aseptic connector assembly 63, though in some embodiments there may be. The upper aseptic connector 80 includes a wide, circular base 82 and the projecting post 83 extending coaxially from the base 82. The post 83 has outwardly-directed threads 84, which, as shown in FIG. 4, correspond to and engage with the inwardly-formed thread 73 on the tip 72 of the reservoir 23. A bore 85 is formed through the post 83 and reduces in diameter to a hole 86 through the base 82, providing a pathway for movement of fluid through the upper aseptic connector 80. When engaged with the medicament reservoir 23 as shown in FIG. 4, therefore, the reservoir 23 is coupled in fluid communication with the upper aseptic connector 80 to convey medicament therethrough.

A cylindrical, coaxial seat 90 is formed into a lower face 91 of the upper aseptic connector 80 opposite the post 83. The seat 90 communicates with the hole 86. An annular gasket 92 is received in the seat 90, the inner diameter of which is commensurate with that of the hole 86. The gasket 92 has a height just slightly greater than the depth of the seat 90, so that the gasket 92 protrudes slightly beyond the lower face 91. The gasket 92 is constructed from a material or combination of materials having characteristics of inertness, low permeability, durability, and compressibility, such as rubber. A thin film 93 is applied over the gasket 92 and is adhered and sealed to the lower face 91 of the upper aseptic connector 80. The thin film 93 completely overlies the gasket 92 with a continuous, closed-loop seal formed between the thin film 93 and the lower face 91 to act as a barrier to fluid migration.

The lower aseptic connector 81 is similar, but not identical, to the upper aseptic connector 80. Still referring to FIG. 4, the lower aseptic connector 81 includes a wide, circular base 94 and a projecting post 95 carrying a barb fitting 100, the post 95 extending coaxially from the base 94. The base 94 is coextensive to the base 82, having a similar outer diameter as the base 82 and a similar thickness. The post 95 is narrower than the post 83 of the upper aseptic connector 80, and has a bore 101 which is reduced in diameter in comparison to the bore 85 in the post 83 of the upper aseptic connector 80. The bore 101 is roughly equal in diameter to the hole 86 in the upper aseptic connector 80. As shown in FIG. 4, a major tubing 120 of the tubing set 64 is fit over the barb fitting 100 and has an inner diameter commensurate with the diameter of the bore 101, providing a pathway for movement of fluid out of the lower aseptic connector 81 into the tubing set 64 to convey medicament therethrough.

A cylindrical, coaxial seat 102 is formed into an upper face 103 of the lower aseptic connector 81 opposite the post 95. The seat 102 communicates with the bore 101. An annular gasket 104 is received in the seat 102, the inner diameter of which is commensurate with that of the bore 101. The gasket 104 is constructed from a material or combination of materials having characteristics of inertness, low permeability, durability, and compressibility, such as rubber. The gasket 104 has a height just slightly greater than the depth of the seat 102, so that the gasket 104 protrudes slightly beyond the upper face 103. A thin film 105 is applied over the gasket 104 and is adhered and sealed to the upper face 103 of the lower aseptic connector 81. The thin film 105 completely overlies the gasket 104 with a continuous, closed-loop seal formed between the thin film 105 and the upper face 103 to act as a barrier to fluid migration. One having ordinary skill in the art will understand that the thin film 93 may be identified as a "first thin film" and the thin film 105 may be identified as a "second thin film," and that such designations do not limit the number of thin films of the device 10. Similarly, one having ordinary skill in the art will understand that the bore 85, seat 90, and gasket 92 may be identified as a "first bore," "first seat," and "first gasket," and that the bore 101, seat 102, and gasket 104 may be identified as a "second bore," "second seat," and "second gasket," and that such designations do not limit the number of bores, seats, or gaskets of the device 10.

The upper and lower aseptic connectors 80 and 81 form a sterile fitting between the medicament reservoir 23 and the tubing set 64 allowing the reservoir 23 to be sterilized separately from the tubing 64 and then attached to the sterile tubing without affecting the sterility of either. Referring still to FIG. 4, four fingers 110 project axially from the periphery of the base 94, each terminating in an enlarged, radially inwardly-directed head 111. The fingers 110 couple and hold the upper and lower aseptic connectors 80 and 81 together in coaxial alignment. The fingers 110 are circumferentially spaced apart around the upper and lower aseptic connectors 80 and 81, further maintaining coaxial alignment between the upper and lower aseptic connectors 80 and 81. When the upper and lower aseptic connectors 80 and 81 are coupled together, the heads 111 of the fingers 110 fit over an upper face 112 of the upper aseptic connector 80, and the fingers 110 compress the upper and lower aseptic connectors 80 and 81 together. With the upper and lower aseptic connectors 80 and 81 aligned and compressed together, the bores 85 and 101 are coaxially aligned, the gaskets 92 and 104 are coaxially aligned and compressed toward each other, defining a continuous circular contact location between the upper and lower aseptic connectors 80 and 81. Between the gaskets 92 and 104 are the two thin films 93 and 105, which are elongate, long, and cooperate to form the two plies of the two-ply ribbon 53 of the pull assembly 51 described in reference to FIG. 2. As such, the thin films 93 and 105 are each barriers carried by the upper and lower aseptic connectors 80 and 81, respectively, of the aseptic connector assembly 63 and which extend from the aseptic connector assembly 63 to outside of the housing 10. Therefore, the thin films 93 and 105 are barriers of the upper and lower aseptic connectors 80 and 81, respectively, and each is also a barrier of, and carried by, the aseptic connector assembly 63. The thin films 93 and 105 are joined at distal, external ends at the pull tab 54, shown in FIG. 2. The pull tab 54 is an enlarged or rigid member suitable for being easily gasped and pulled such as by the fingers. Thus, in FIG. 4, though the aseptic connector assembly 63 is shown assembled, it is shown in a storage state of the device 10, in which fluid may not yet flow through the aseptic connector assembly 63 for movement from the reservoir 23 into the tubing set 64. Placing the device 10 into the operation state requires at least irreversibly removing the barrier of the thin films 93 and 105 from the aseptic connector assembly 63 irreversibly to join the upper and lower aseptic connectors 80 and 81 in fluid communication. Arranging the device 10 from the storage state to the operation state will be described in further detail below.

Proximate to the slit 52 formed in the seam 45 between the rear top and rear bottom panels 15 and 16, a switch assembly 65 is carried. The switch assembly 65 is disposed on opposed sides of the two-ply ribbon 53. The switch assembly 65 is open when the two-ply ribbon 53 is interposed through the switch assembly 65, and the switch assembly 65 is closed when the two-ply ribbon 53 is not interposed through the switch assembly 65. Preferably, the switch assembly 65 includes an upper electrical contact 65a and a lower electrical contact 65b. The two-ply ribbon 53 is constructed of a non-conductive material, and so when the two-ply ribbon 53 is interposed between the upper and lower electrical contacts 65a and 65b, electrical communication between the upper and lower electrical contacts 65a and 65b is prevented. When the two-ply ribbon 53 is removed, such as would occur when the device 10 is moved from the storage state to the operational state by a medical professional pulling the two-ply ribbon 53 out of the device 10, the upper and lower electrical contacts 65a and 65b are placed in contact with each other and are coupled in electrical communication. Coupling the upper and lower electrical contacts 65a and 65b in electrical communication closes the switch assembly 65 and energizes the device 10.

Figure 5:
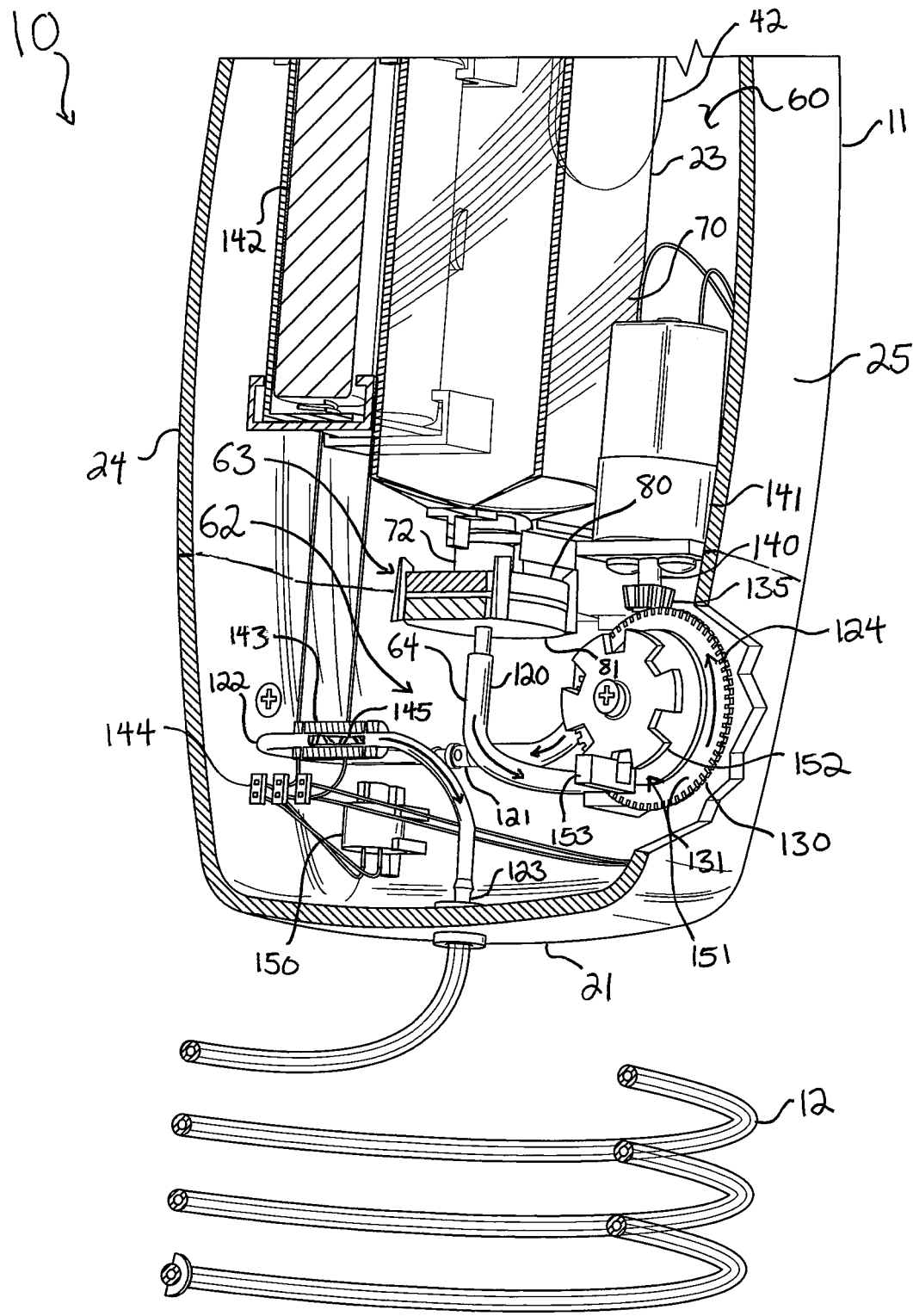
FIG. 5 is an alternate perspective of a section view of the device of FIG. 1 taken along the line 3-3 in FIG. 1.

Turning now to FIG. 5, which is a perspective view taken along the section line 3-3 in FIG. 1, the tubing set 64 is shown. The tubing set 64 includes the major tubing 120 having a first diameter, minor tubing 122 having a second diameter less than the first diameter of the major tubing 120, and a reducing coupler 121 coupling the major tubing 120 to the minor tubing 122. The tubing set 64 additionally includes a strain-relief coupling 123 extending through the housing 11 at the bottom 21, to which the administration line 12 is coupled and extends therefrom.

Figure 6:
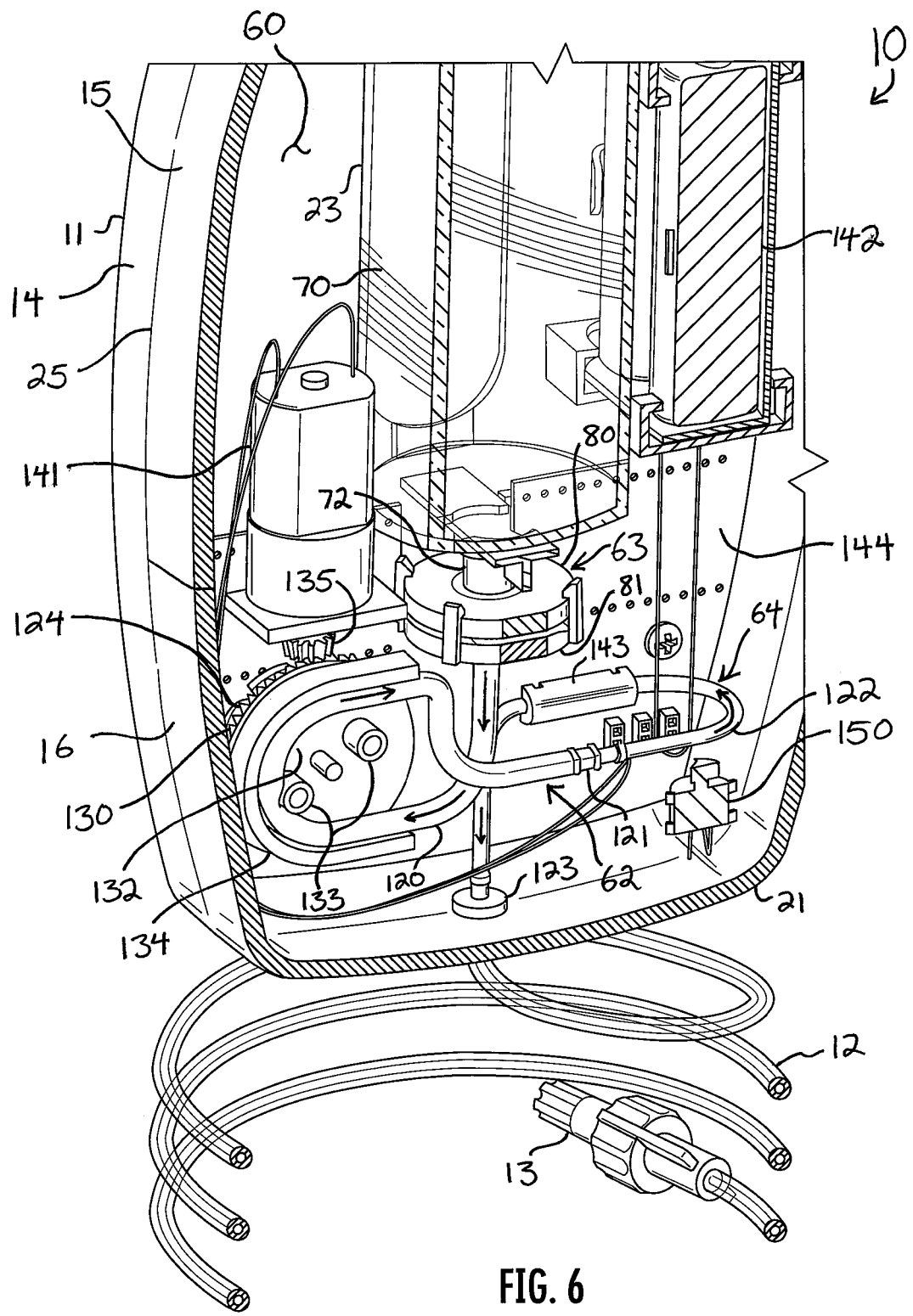
FIG. 6 is a section view of the device of FIG. 1 taken along the line 6-6 in FIG. 2.

The major tubing 120 is constructed of a material or combination of materials having characteristics of flexibility, fluid impermeability, and compressibility, such as polyvinylchloride, polyurethane, silicone, or the like. The major tubing 120 is routed around a pump unit 124 which acts on the major tubing 120 to draw medicament through the major tubing 120 from the reservoir 23. Referring to FIG. 5 and to FIG. 6, which is a section view taken along line 6-6 in FIG. 2, and which illustrates the interior 60 of the housing 11 at a roughly opposed angle from that of FIG. 5, the pump unit 124 includes a bevel gear wheel 130 mounted for rotation about a central axis of rotation and having a front face 131 and a rear face 132. Rollers 133 are mounted to the rear face 132 and extend backward (toward the bottom rear panel 16) parallel to the axis of rotation of the bevel gear wheel 130. FIG. 6 shows an embodiment in which there are two rollers 133, but there may be three or four rollers 133 in other embodiments. The rollers 133 are shafts mounted to the bevel gear wheel 130 and rotate to impinge and compress the major tubing 120 against an arcuate, roughly semicircular wall 134. As the bevel gear wheel 130 rotates, the rollers 133 compress the major tubing 120 to occlude the major tubing 120. When the bevel gear wheel 130 is rotated so that two rollers 133 compress the major tubing 130, liquid medicament is trapped in the major tubing 120 between the two rollers 133 so that a certain volume of medicament is controllably withheld in the major tubing 120 and then released downstream when the leading roller 130 stops compressing the major tubing 120.

Referring still to FIGS. 5 and 6, the bevel gear wheel 130 is rotated by a drive bevel gear 135 which is fitted on a shaft 140 extending from a motor 141. The motor 141 is a DC or step motor powered by a battery supply 142 carried within the housing 11. The motor 141 rotates the shaft 140 and the drive bevel gear 135, which meshingly engages with the bevel gear wheel 130 to rotate the bevel gear wheel 130, and thereby rotate the rollers into and out of impingement with the major tubing 120.

Referring to both FIGS. 5 and 6 still, the major tubing 120 extends from the pump unit 124 to a reducing coupler 121, which transitions the larger first diameter of the major tubing 120 to the smaller second diameter of the minor tubing 122. The minor tubing 122 bends around to just behind the front panel 14 where it passes through a constricting channel 143. The constricting channel 143 is a rigid, elongate, semi-cylindrical structure secured to a printed circuit board 144 (the backside of which is seen in FIG. 6). The constricting channel 143 has an inner diameter equal to the outer diameter of the minor tubing 122 and prevents the minor tubing 122 from swelling or expanding radially. A force-sensing resistor 145 is disposed on the printed circuit board 144 at the constriction channel 143, so that the minor tubing 122 is in direct contact with the force-sensing resister 145 when routed through the constriction channel 143. The force-sensing resistor 145 is coupled in electrical communication to logic carried on the printed circuit board 144. The force-sensing resistor 145 measures a compressive force acting on it, and with the logic on the printed circuit board 144, determines the extent of swelling or radial expansion in the minor tubing. In some embodiments, the minor tubing 122 has a thin sidewall, allowing for more precise measurements of force.

From the force-sensing resistor 145, the minor tubing 122 bends downward and into the strain-relief coupling 123, to which the administration line 12 is coupled. The administration line 12 is a long, flexible, tubing terminating in the coupling 13, which is a luer fitting or the like, and is capped to maintain the sterility of the administration line 12.

A medical professional preparing the device 10 for use with a patient obtains the device 10 in a preferably packaged state. The device 10, including the housing 11, the components within the housing 11, and the administration line 12, are contained within the packaging. Such packaging need not necessarily be a sterilized packaging, given that the fluid communication path 62 was previously sterilized before assembly and will thus be sterile upon the opening of the packaging by the medical professional. The fluid communication path 62, being composed of the medicament reservoir 23, the aseptic connector assembly 63, the tubing set 64, and the administration line 12, is sterilized in two separate steps. In one step, the upper aseptic connector 80 is applied to the tip 72 of the reservoir 23. The upper aseptic connector 80, with its thin film 93 applied, prevents medicament from prematurely discharging from the reservoir 23. The medicament reservoir 23 is filled with a liquid medicament and then terminally sterilized by steam autoclave, together with the upper aseptic connector 80. In one manner of filling the medicament reservoir 23 with liquid medicament, the piston 74 is inserted into the barrel 70, which is open at the tip 72. Liquid medicament is supplied to the barrel 70 and the barrel 70 is then capped with the upper aseptic connector 80. In another manner of filling the medicament reservoir 23 with liquid medicament, the barrel 70 is capped with upper aseptic connector 80 at the tip 72, the liquid medicament is supplied to the barrel 70, and the piston 74 is then inserted into the barrel 70. The medicament reservoir 23 and the upper aseptic connector 80 together thus present a first sterilized part for assembly into the fluid communication path 62.

The lower aseptic connector 81, the tubing set 64, and the administration line 12 are sterilized independently from the medicament reservoir 23 and the upper aseptic connector 80. The major tubing 120 of the tubing set 64 is securely press fit onto the barb fitting 100 of the lower aseptic connector 81. One end of the reducing coupler 121 is then press fit into the major tubing 120, and the minor tubing 122 is press-fit over an opposed of the reducing coupler 121. The strain relief coupling 123 is fit into the free end of the minor tubing 122, and the administration line 12 is fit onto the strain relief coupling 123. The administration line 12 terminates with the coupling 13, which is preferably a luer fitting. Between the luer fitting coupling 13 and the thin film 105 on the upper aseptic connector 81, the tubing set 64 defines a closed system. The tubing set 64, the lower aseptic connector 81, and the administration line 12 are sterilized by Gamma radiation exposure and then applied into the housing 11. In some embodiments, the tubing set 64 assembled as described above will first be applied into the housing 11 and routed through the housing 11 and the pump unit 124, and then sterilized with exposure to Gamma radiation or ethylene oxide gas. In both manners, the medicament reservoir 23 and the upper aseptic connector 80 are sterilized separately from the lower aseptic connector 81, the tubing set 64, and the administration line 12.

With the medicament reservoir 23 and the upper aseptic connector 80 sterile, and with the lower aseptic connector 81, tubing set 64, and administration line 12 sterile, the fluid communication path 62 is ready for assembly by coupling and irreversibly engaging the upper and lower aseptic connectors 80 and 81, thus forming the aseptic connector assembly 63 installed and shown throughout the drawings. When the aseptic connector assembly 63 is formed, the two-ply ribbon 53 is threaded through the slit 52 in the housing 11, and the pull tab 54 is crimped, glued, or otherwise secured to the distal end of the two-ply ribbon 53. Once assembled in this manner, the sterility of the fluid communication path 62 is maintained and protected. The device 10 is then ready for shipping through distribution to medical professionals.

When a medical professional prepares the device 10 for use, the medical professional selects the device 10 containing the medicament needed for the procedure. For example, if Propofol must be administered to the patient, the medical professional obtains a device 10 containing Propofol. Alternatively, if Dexmedetomidine must be administered to the patient, the medical professional obtains a device 10 containing Dexmedetomidine. It is noted here that the device 10 is effective at delivering a variety of drug products, including liquid medicaments, and including, but not limited to Ofirmev® (Acetaminophen), Ketamine, Propofol, Precedex® (Dexmedetomidine), Fentanyl, Remifentanyl, Etomidate, Midazolam, Cubicin® (Daptomycin), Invanz® (Ertapenem), Polymyxin B, Acyclovir, Amikacin, Amphotericin B, Chloramphenicol, Vistide® (Cidofovir), Doxycycline, Erythromycin, Gentamicin, Synercid® (Quinupristin and Dalfopristin), Rifampin, Timentin® (Ticarcillin and Clavulanate), Tobramycin, Avastin® (Bevacizumab), Herceptin® (Trastuzumab), Cytoxan® (Cyclophosphamide), Neupogen® (Filgrastim), Vectibix® (Panitumumab), Cladribine, Dacarbazine, Remicade® (Infliximab), Foscarnet, Ganciclovir, Cerezyme® (Imiglucerase), Elelyso® (Taliglucerase alfa), Vpriv® (Velaglucerase alfa), Granisetron, Dopamine, Norepinephrine, Dobutamine, Milrinone, TPN (Total Parenteral Nutrition), IVIG (Intravenous Immunoglobulin), Gammagard® (Immune Globulin), Amrinone® (Inamrinone), Deferoxamine, Hemin, and Sodium Valproate, each of which is a medicament for which the dosage is set and administered depending on the weight of the patient. The device 10 is also effective at delivering a variety of drug products, including liquid medicaments, for which the dosage is set and administered depending on the height or surface area of a patient, including, but not limited to Azactam® (Aztreonam), Trimetrexate, 5FU (5-Fluorouracil), Rituxan® (Rituximab), Bleomycin, Erbitux® (Cetuximab), Velcade® (Vortezomib), Mylotarg® (Gemtuzumab Ozogamicin), Zevalin® (Ibritumomab Tiuxetan), Epirubicin, Fludarabine, Gemcitabine, Irinotecan, Oxalaplatin, Paclitaxel, Topotecan, Vinorelbine, Carboplatin, Carmustine, Cisplatin, Daunorubicin, Dexrazoxane, Docetaxel, Doxorubicin, Etoposide, Idarubicin, Ifosfamide, Camptosar, Mitomycin, Mitoxantrone, Leukine® (Sargramostim), Streptozocin, Vumon® (Teniposide), and Vinblastine.

After selecting the appropriate device 10, the medical professional removes the device 10 from its packaging and arranges the device 10 for use, such as by hanging from the hook 61 off of a stand proximate to the patient. The cap on the coupling 13 is removed and connected to a catheter already secured to the patient. In this manner, the fluid communication path 62 is coupled to the catheter on the patient with minimal opportunity for contamination. The medical professional then operates the device 10.

The device 10 is shipped in the storage state. In the storage state, the fluid communication path 62 is sterile and closed, but occluded by the thin films 93 and 105 on the upper and lower aseptic connectors 80 and 81. Further, in the storage state, the device 10 is not energized: no power is provided to the printed circuit board 144 or the motor 141, and the printed circuit board 144 or the motor 141 are electrically isolated from the battery supply 142. To operate the device 10, the medical professional must first both energize the device 10 and remove this occlusion. Energizing the device 10 is accomplished by pulling on the two-ply ribbon 53 to remove the two-ply ribbon 53, which simultaneously removes the occlusion. As the two-ply ribbon 53, consisting of both thin films 93 and 105, is drawn out of the housing, the thin films 93 and 105 are peeled off of the lower and upper faces 91 and 103, respectively, of the upper and lower aseptic connectors 80 and 81, respectively. Once the thin films 93 and 105 are removed from between the upper and lower aseptic connectors 80 and 81, the gaskets 92 and 104 are in direct and sealing contact with each other, still biased into compression with each other by the fingers 110. With the upper and lower aseptic connectors 80 and 81 maintained in coaxial alignment by the fingers 110, and the gaskets 92 and 104 thus maintained in coaxial alignment, the hole 86 in the upper aseptic connector 80 is coupled in fluid communication with the bore 101 of the lower aseptic connector 81.

In response to the two-ply ribbon 53 being removed from the housing 11, the upper and lower electrical contacts 65a and 65b proximate the aseptic connector assembly 63 are coupled, the switch assembly 65 is closed, and power is made available to the pump unit 124 from the battery supply 142. The printed circuit board 144 and the motor 141 are electrically coupled to the battery supply 142, and power is provided to the printed circuit board 144 and the motor 141. The device 10 is then ready for operation by the medical professional.

Depending on the medicament being administered to the patient, the medical professional will operate the pair of buttons 33 on the left side 24 of the device 10 and the pair of buttons 41 on the right side 25 of the device 10. If the medicament is one for which the dosage is dependent on weight, the medical professional will operate the pair of buttons 33 on the left side 24 of the device 10, incrementing or decrementing a weight value shown in the display 34 until it corresponds to the patient. Subsequently, the medical professional will operate the pair of buttons 41 on the right side 25 of the device 10, incrementing or decrementing a dosage value shown in the display 42 until it corresponds to the patient. Each time one of the buttons of the pair of buttons 33 or 41 is depressed, tactile, haptic or audible feedback is preferably provided to the medical professional. As seen in FIGS. 5 and 6, a small eccentric motor 150 is mounted in the interior 60 of the housing 11 and coupled to the battery supply 142 and the printed circuit board 144. In response to the one of the buttons of the pair of buttons 33 or 41 being depressed, the eccentric motor 150 rotates an eccentric or off-center mass to provide a small feedback pulse or vibration indicating to the medical professional that the button has been pressed.

Prior to connecting the device 10 to the patient for administration of the liquid medicament, the device 10 is preferably primed to remove any air from the fluid communication path 64. This can be accomplished by depressing the bolus button 44. Once the medical professional has set the device 10 to properly administer the medicament to the patient and the administration line 12 is properly connected to the patient, the medical professional depresses either the start/stop button 43 or the bolus button 44 to initiate operation of the device 10. The start/stop button 43 overlies and is electrically connected to the printed circuit board 144, and the logic on the printed circuit board 144 instructs the motor 141 to begin rotating. Depressing the start/stop button 43 once causes the printed circuit board 144 to issue an instruction to the motor 141 to begin rotating. Similarly, the bolus button 44 overlies and is electrically connected to the printed circuit board 144, and the logic on the printed circuit board 144 instructs the motor 141 to begin rotating according to a predetermined operation for administering a bolus volume of medicament. Depressing the bolus button 44 once causes the printed circuit board 144 to issue an instruction to the motor 141 to begin rotating.

The motor 141 rotates at a speed determined by the logic on the printed circuit board 144 based on the parameters displayed by windows 34 and 42 selected by the medical professional. Referring now to FIGS. 5 and 6, rotation of the motor 141 causes the bevel gear wheel 130 to rotate. The rotational speed of the bevel gear wheel 130 is monitored by an optical sensor assembly 151. The optical sensor assembly 151 includes a slotted wheel 152 mounted coaxially for rotation with the bevel gear wheel 130, and an optical sensor 153 mounted over the slotted wheel 152. The slotted wheel 152 is a cylindrical disc formed with a plurality of circumferentially-spaced apart notches extending radially into the slotted wheel 152. The optical sensor assembly 151 has a transmitter and a receiver disposed on opposed sides of the slotted wheel 152, and the transmitter emits an optical signal consisting of electromagnetic radiation across to the receiver. When the slotted wheel 152 is interposed between the transmitter and receiver, the optical signal is blocked and the receiver records nothing. When one of the notches on the slotted wheel 152 is disposed between the transmitter and receiver, however, the optical signal is received and the receiver records the receipt. Hence, the optical sensor 153 records a series of interspersed, sequential receipts of the optical signal, and because the width of the notches is known, the optical sensor 153 can count the number of successful receipts and the duration of such receipts, so that the logic on the printed circuit board 144 can determine how quickly the bevel gear wheel 130 is rotating. This, in turn, allows the logic on the printed circuit board 144 to determine the rate at which medicament is being supplied to the patient, in comparison with the selected dosage rate.

Medicament is thus communicated through the major tubing 120 around the pump unit 124. The pump unit 124 draws medicament through the major tubing 120. In so doing, the downstream pump unit 124 applies a negative pressure in the major tubing 120 to draw medicament out of the reservoir 23. The pump unit 124 thus pulls medicament out of the reservoir 23 and through the major tubing 120. The pump unit 124 further pushes medicament out of the major tubing 120, into the minor tubing 122, and out the administration line 12 to the patient.

A preferred embodiment is fully and clearly described above so as to enable one having skill in the art to understand, make, and use the same. Those skilled in the art will recognize that modifications may be made to the described embodiment without departing from the spirit of the invention. To the extent that such modifications do not depart from the spirit of the invention, they are intended to be included within the scope thereof.

The invention claimed is:

1. A method of assembling a liquid medicament dispenser, comprising the steps of:
providing a housing, a reservoir, a tubing set, an administration line, an aseptic connector assembly separated into upstream and downstream portions, and a pump;

coupling the upstream portion of the aseptic connector assembly to the reservoir;

filling the reservoir with a liquid medicament;

coupling the downstream portion of the aseptic connector assembly to the tubing set;

sterilizing together the reservoir and the upstream portion of the aseptic connector assembly;

sterilizing together the downstream portion of the aseptic connector assembly, the tubing set, and the administration line independently from the step of sterilizing together the reservoir and the upstream portion of the aseptic connector assembly;

providing a barrier, and interposing the barrier between the upstream and downstream portions of the aseptic connector assembly;

connecting the upstream portion of the aseptic connector assembly to the downstream portion of the aseptic connector assembly;

mounting the reservoir and the pump in the housing;

providing a pull assembly coupled to the barrier, and routing the pull assembly through the housing so as to extend outside the housing; and routing the tubing set in the housing, around the pump, and through an outlet in the housing, so that the administration line extends outside of the housing.

2. The method of claim 1, wherein the aseptic connector assembly further comprises:

a first bore in the upstream portion of the aseptic connector assembly and a first seat around the first bore;

a second bore in the downstream portion of the aseptic connector assembly and a second seat around the second bore;

first and second gaskets, each seated in the respective first and second seats of the respective upstream and downstream portions of the aseptic connector assembly; and the step of interposing further comprises disposing the barrier between the first and second gaskets.

3. The method of claim 2, wherein the step of connecting the upstream portion of the aseptic connector assembly to the downstream portion of the aseptic connector assembly further comprises:

aligning the first and second bores, and the first and second gaskets, of the upstream and downstream portions, respectively, with each other; and applying the upstream portion of the aseptic connector assembly to the downstream portion of the aseptic connector assembly with the first and second gaskets disposed therebetween, forming a sterile passageway through the aseptic connector assembly from the reservoir to the tubing set.

4. The method of claim 1, wherein the barrier is irreversibly removable from the aseptic connector assembly.

5. The method of claim 1, further comprising:

providing a switch assembly for energizing the dispenser in a closed state of the switch assembly; and operatively coupling the switch assembly to the barrier so that removal of the barrier from the aseptic connector assembly places the switch assembly in the closed state thereof.

6. The method of claim 1, further comprising the steps of:

providing a printed circuit board carrying a pressure sensitive resistor; and routing the tubing set against the pressure sensitive resistor.

* * * * *